United States Patent

Cremer et al.

Patent Number: 5,457,112
Date of Patent: Oct. 10, 1995

[54] 3-(6-QUINOLYLMETHYL)-4H-IMIDAZOL-4-ONE DERIVATIVES, THEIR PREPARATION AND THEIR APPLICATION IN THERAPY

[75] Inventors: Gérard Cremer, Morangis; Jean Claude Muller, Morsang S/Orge, both of France

[73] Assignee: Synthelabo, Le Plessis Robinson, France

[21] Appl. No.: 165,648

[22] Filed: Dec. 13, 1993

Related U.S. Application Data

[63] Continuation-in-part of Ser. No. 2,502, Jan. 6, 1993, abandoned.

[30] Foreign Application Priority Data

Dec. 14, 1992 [FR] France ................... 92 15038

[51] Int. Cl.⁶ ................... C07D 215/04; A61K 31/47
[52] U.S. Cl. ................... 514/314; 546/173; 514/278
[58] Field of Search ................... 546/173; 514/314

OTHER PUBLICATIONS

D. J. Carini et al., Journal of Medicinal Chemistry, vol. 33, No. 5, 1990, pp. 1330–1336.

Primary Examiner—Gary L. Geist
Assistant Examiner—Catherine S. Scalzo Kilby
Attorney, Agent, or Firm—Jacobson, Price, Holman & Stern

[57] ABSTRACT 3-(6-Quinolylmethyl)-4H-imidazol-4-one derivatives corresponding to the formula (I):

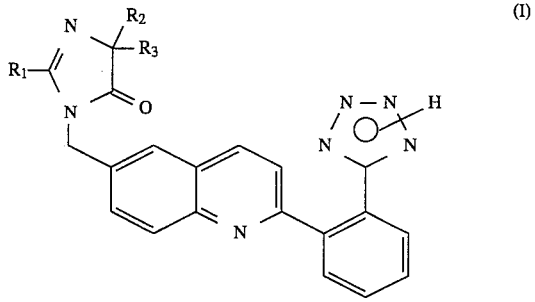

in which
$R_1$ represents an unbranched or branched ($C_2$–$C_5$) alkyl group,
$R_2$ and $R_3$ represent, each independently of one another, either a hydrogen atom, or an unbranched or branched ($C_1$–$C_5$)alkyl group, or a $(CH_2)_n$-aryl group where n=0 to 3, or $R_2$ and $R_3$ with the imidazole ring can form a spirocyclo($C_3$–$C_8$)alkyl group,
as well as their addition salts with pharmaceutically acceptable acids and bases.

8 Claims, No Drawings

3-(6-QUINOLYLMETHYL)-4H-IMIDAZOL-4-ONE DERIVATIVES, THEIR PREPARATION AND THEIR APPLICATION IN THERAPY

This is a continuation-in-part of application Ser. No. 08/002,502, filed Jan. 6, 1993, abandoned.

The present invention relates to 3-(6-quinolylmethyl)-4H-imidazol-4-one derivatives, to their preparation and to their application in therapy.

The compounds of the invention correspond to the formula (I)

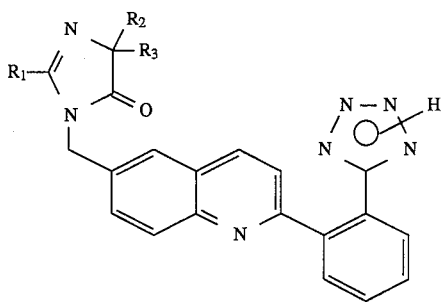

in which $R_1$ represents an unbranched or branched $(C_2$–$C_5)$alkyl group, $R_2$ and $R_3$ represent, each independently of one another, either a hydrogen atom, or an unbranched or branched $(C_1$–$C_5)$alkyl group, or a $(CH_2)_n$-aryl group where n=0 to 3, or $R_2$ and $R_3$ with the imidazole ring can form a spirocyclo($C_3$–$C_8$) alkyl group.

The preferred compounds of the invention are compounds having formula (I) wherein, $R_1$ represents an unbranched or branched $(C_2$–$C_5)$alkyl group, $R_2$ and $R_3$ represent, each independently of one another, an unbranched or branched $(C_1$–$C_5)$alkyl group, or $R_2$ and $R_3$ with the imidazole ring can form a spirocyclo $(C_3$–$C_8)$ alkyl group.

Among them the compounds of choice are those having formula (I) wherein, $R_1$ represents a butyl group, $R_2$ and $R_3$ represent, each independently of one another, an unbranched or branched $(C_1$–$C_5)$alkyl group, or $R_2$ and $R_3$ with the imidazole ring can form a spirocyclo $(C_3$–$C_8)$ alkyl group.

The compounds of the invention may be presented in free form or in the form of pharmaceutically acceptable organic or inorganic salts.

According to the invention, the compounds of formula (I) may be synthesized according to Scheme 1.

4-Methylbenzenamine (para-toluidine) is reacted at the refluxing temperature with a benzaldehyde of formula (II), in which X represents a bromine or iodine atom, in the presence of a catalyst such as 4-methylbenzenesulfonic acid (para-toluenesulfonic acid), in solution in benzene. After cooling, propiolic acid is added and the mixture is heated to the refluxing temperature so as to obtain the compound of formula (III). Next, a mixture of the compound of formula (III) and cuprous cyanide is heated in a solvent such as pyridine so as to obtain 2-(6-methyl-2-quinolyl)benzonitrile (IV), which is reacted with an organometallic azide such as trimethyltin azide, or a metal azide such as sodium azide, so as to obtain a compound over which a stream of gaseous hydrochloric acid is passed in order to obtain the quinoline of formula (V). The first reaction is performed in a solvent such as xylene at the refluxing temperature; the second reaction is performed in a solvent such as a toluene/tetrahydrofuran mixture at room temperature.

The tetrazole group of the quinoline of formula (V) is then protected with a protective group $R_4$, where $R_4$

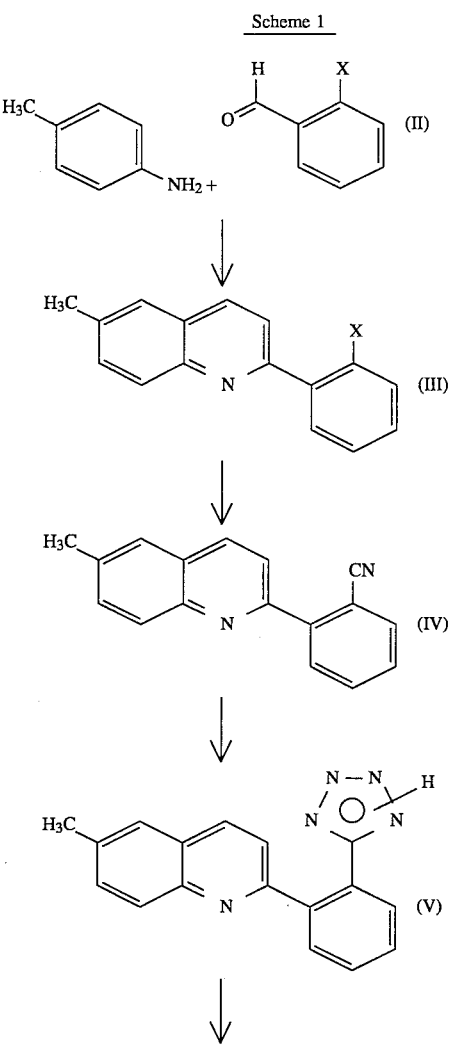

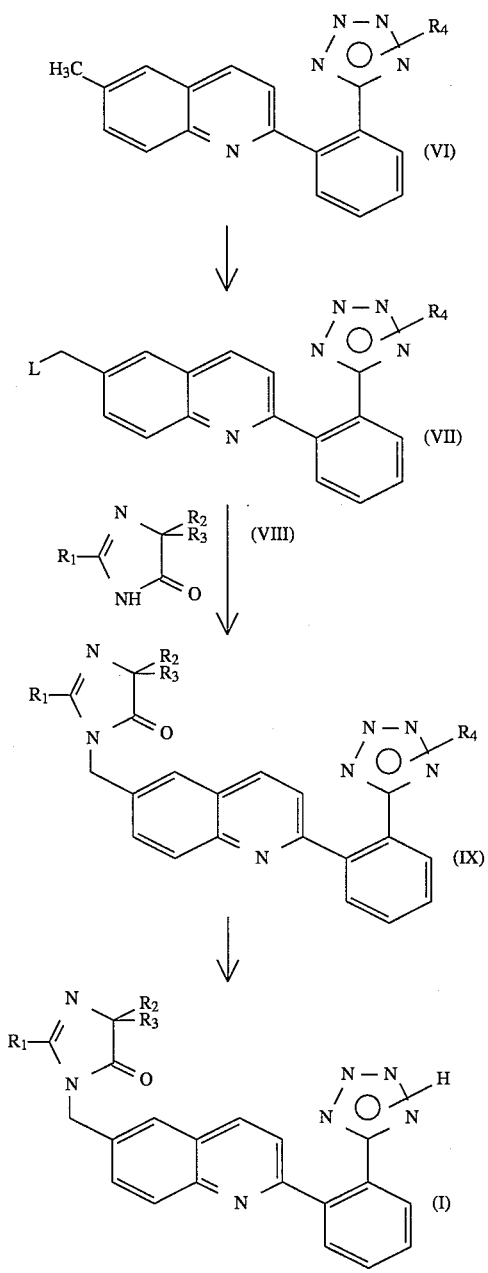

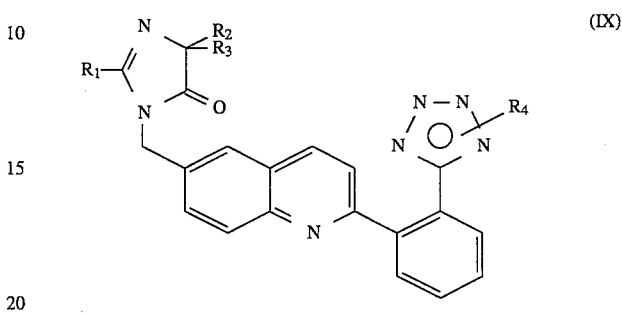

formula (VII) is condensed, in dimethylformamide at a temperature of 0° C. to 50° C., in the presence of a base such as potassium hydroxide or potassium carbonate, with an imidazolone of formula (VIII) in which $R_1$, $R_2$ and $R_3$ are as defined above, and a compound of formula (IX) is obtained, which compound is subjected to deprotection.

The compounds of formula (IX)

in which $R_1$, $R_2$, $R_3$ and $R_4$ are as defined above, are new and form part of the invention.

The starting compounds are commercially available or described in the literature, or may be prepared according to methods which are described therein or which are known to those skilled in the art.

Thus, the imidazolones of formula (VIII) may be synthesized according to the method described by Jacquier et al (Bull. Soc. Chim. France, 1971, 3, 1040–1051), by condensation of an alkyl imidate and an amino acid ester such as, for example, methyl 1-amino-1-cyclopropylcarboxylate.

Methyl 1-amino-1-cyclopropylcarboxylate is prepared according to the method described by Valdyanathan (J. Org. Chem., 1989, 54, 1810–1815).

The compounds of formula (VII) are prepared according to the method described in the European Patent Application published under No. 0540400 by the Applicant.

The examples which follow illustrate the invention.

The microanalyses and the IR and NMR spectra confirm the structure of the compounds obtained.

represents a group of formula $CR_5R_6R_7$ in which $R_5$, $R_6$ and $R_7$ are, each independently of one another, a $(C_1-C_2)$alkyl group or an aryl group; in this step, the compound (V) is reacted with a protective agent such as, for example, trityl chloride at room temperature in a solvent such as dichloromethane, in the presence of a base such as N-methylmorpholine or triethylamine, and a compound of formula (VI) in which $R_5$, $R_6$ and $R_7$ are as defined above is obtained. Next, the methyl group at position 6 of the quinoline of formula (VI) is functionalized by introducing a leaving group L, for example a bromo radical, into it, and a compound of formula (VII) where $R_5$, $R_6$ and $R_7$ are as defined above is obtained; the reaction is performed at the refluxing temperature in a solvent such as carbon tetrachloride, in the presence of an initiator such as benzoyl peroxide or α,α'-azobisisobutyronitrile, at the refluxing temperature. Finally, the compound of

EXAMPLE 1

5-butyl-6-[[2-[2-(1H-tetrazol-5-yl]phenyl]-6-quinolyl]methyl] -4,6-diazaspiro[2.4]hept-4-en-7-one 1.1. 6-bromomethyl-2-[2-[2-((triphenylmethyl)2H-tetrazol- 5-yl]phenyl]quinoline 1.1.1. 2-(2-bromophenyl)-6-methylquinoline 50 g (270 mmol) of 2-bromobenzaldehyde are heated to the refluxing temperature, in a round-bottomed flask surmounted by a Dean and Stark apparatus, with 29.5 g (276 mmol) of para-toluidine and 0.5 g of para-toluenesulfonic acid dissolved in one liter of benzene. When the removal of water is complete (approximately 5 ml), 8.3 ml (135 mmol) of propiolic acid are added to the reaction medium which has been cooled beforehand to about 50° C. A substantial evolution of $CO_2$ is noted, and the mixture is brought to reflux for 3 hours. The reaction is monitored by thin-layer chromatography in a mixture of dichloromethane and hexane (70:30) . Under these experimental conditions, it has been necessary to add a 20% excess of propiolic acid followed by 1 hour of reflux in order to complete the reaction. The solvent is evaporated off under reduced pressure and the residue is purified by chromatography on a silica column, eluting with a mixture of dichloromethane and hexane (70:30).

22 g of the expected derivative are recovered in the form of a crystallized compound.

M=22 g $^1$H NMR (200 MHz, CDCl$_3$): δ 2.55 (s, 3H), 7.25–7.70 (m, 7H), 8.02–8.15 (m, 2H).

In the same manner, 2-(2-iodophenyl)-6-methylquinoline is prepared from 2-iodobenzaldehyde.

M.p.=77°–77.5° C.

1.1.2. 2-(6-methyl-2-quinolyl)benzonitrile

A mixture containing 15 g (50 mmol) of the compound obtained above in 1.1.1 and 5 g (56 mmol) of cuprous cyanide is heated to 160° C. for 12 hours, under argon, in 60 ml of pyridine. The reaction is monitored by thin-layer chromatography in dichloromethane. The pyridine is evaporated off under reduced pressure and the residue is taken up with dichloromethane. The organic phase is washed several times with aqueous ammonia solution until the aqueous phase is colorless. After a final wash with water, the organic phase is dried over magnesium sulfate and the solvent is evaporated off. The residue is taken up with petroleum ether.

M=9.6 g M.p.=157° C. Yld=78%

1.1.3. 6-methyl-2-[2-(1H-tetrazol-5-yl)phenyl]quinoline hydrochloride 9.6 g (39.3 mmol) of nitrile obtained above in 1.1.2 and 14.96 g (72.7 mmol) of trimethyltin azide are introduced into 110 ml of xylene. This mixture is brought to reflux for 15 hours. After cooling, the solid is filtered off and suspended in 115 ml of toluene and 7 ml of tetrahydrofuran. The mixture is cooled in an ice bath and subjected to a stream of hydrogen chloride gas bubbled through for 2 hours. The insoluble fraction is recovered by filtration and then washed with toluene and with water.

M=13 g 1.1.4. 6-methyl-2-[2-[1(or 2)-(triphenylmethyl)-1(or 2)H-tetrazol- 5-yl]phenyl]quinoline 80.5 g (219 mmol) of the compound obtained above in 1.1.3, 60 ml (547 mmol) of N-methylmorpholine and 73.1 g (262 mmol) of trityl chloride are added at room temperature to one liter of dichloromethane. The solution is stirred overnight and taken up with water, and the organic phase is washed twice with water and then dried. The solvent is evaporated off and the residue is crystallized in a minimum amount of ether.

M=119 g M.p.=176°–177° C. Yld=87%

1.1.5. 6-bromomethyl-2-[2-[1(or 2)-(triphenylmethyl)-1(or 2)H-tetrazol-5-yl]phenyl]quinoline 10 g (189 mmol) of the compound obtained above in 1.1.4 are added to 300 ml of carbon tetrachloride, and the mixture is brought to about 60° C. until dissolution is complete. At this temperature, 3.7 g (20.8 mmol) of N-bromosuccinimide and 60 mg (0.37 mmol) of α,α'-azobisisobutyronitrile are added in a single portion. The mixture is brought to the refluxing temperature for 2 to 3 hours until the N-bromosuccinimide has disappeared. 100 ml of water and 300 ml of dichloromethane are added to the cooled mixture. The organic phase is washed several times with water and then dried. The solvent is evaporated off and the residue is ground in diisopropyl ether. A 90% pure product is obtained, which product will be used as it is.

M=10.3 g 1.2. 5-butyl-4,6-diazaspiro[2.4]hept-4-en-7-one hydrochloride

A mixture of 15.6 g (121 mmol) of ethyl pentanimidate and 13.5 g (117.4 mmol) of methyl 1-amino-1-cyclopropylcarboxylate is heated to the refluxing temperature for 8 hours in 150 ml of xylene to which 20 drops of acetic acid are added. The solvent is evaporated off, the residue is taken up with ether and the mixture is acidified with 12N hydrochloric acid. A precipitate is obtained and is filtered off.

$^1$H NMR, 200 MHz(CDCl$_3$) d [sic] 0.95 (t, 3H), 1.45 (m, 2H) 1.6–2.0 (unresolved complex, 4H), 2.20 (m, 2H), 3.0 (t, 2H).

1.3. 5-butyl-6-[[2-[2-[1(or 2)-(triphenylmethyl)-1(or 2)H-tetrazol- 5-yl]phenyl]-6-quinolyl]methyl]-4,6-diaza spiro [2.4] hept-4-en-7-one 1 g (7.24 mmol) of potassium carbonate and 1.42 g (1.87 mmol) of the 80% pure compound obtained above in step 1.1 and 6 ml of dimethylformamide are added to 0.35 g (1.73 mmol) of the hydrochloride obtained in step 1.2. The mixture is left stirring at room temperature overnight. The reaction medium is taken up with water and extracted with dichloromethane. The organic phase is recovered, the solvent is evaporated off and the residue is dried over magnesium sulfate. The residue is purified by chromatography on a column of silica gel, eluting with a toluene/ethyl acetate (80:20) mixture.

1.4. 5-butyl-6-[[2-[2-(1H-tetrazol-5-yl)phenyl]-6-quinolyl] methyl]-4,6-diazaspiro[2.4]hept-4-en-7-one 500 mg of the compound obtained in step 1.3, dissolved in 20 ml of an acetic acid/methanol (90:10) mixture, are heated for 5 hours to the refluxing temperature. The solvents are evaporated off and a gum is obtained, which gum is purified by chromatography on a column of silica gel, eluting with an ethyl acetate/methanol/acetic acid (100:5:0.5) mixture. The product is crystallized in water.

NMR d [sic] 0.77 (t, 3H), 1.17–1.4 (m, 2H), 1.42–1.75 (m, 6H), 2.5 (t, 2H), 4.98 (s, 2H), 7.5–8 (m, 8H), 8.3 (d, 1H), 16.2–16.6 (unresolved complex, 1H).

1.5. 5-butyl-6-[[2-[2-(1H-tetrazol-5-yl)phenyl]6-quinolyl] methyl]-4,6-diazaspiro[2.4]hept-4-en-7-one, dihydrochloride Compound obtained in step 1.3 is dissolved in a minimal volume of ether and 2 equivalents of an aqueous 4N solution of hydrochloric acid are added. The reaction mixture is left stirring at room temperature overnight. The chlorhydride crystallized in the reaction mixture, is filtered and washed with ether.

Melting point=128° C. (decomposition)

EXAMPLE 2

2-butyl-3-[[2-[2-(1H-tetrazol-5-yl)phenyl]-6-quinolyl] methyl] -1,3-diazaspiro[4.4]non-1-en-4-one 2.1. 2-butyl-3-[[2-[2-[1(or 2)-(triphenylmethyl)-1(or 2)H-tetrazol- 5-yl]phenyl]-6-quinolyl]methyl]-1,3-diazaspiro [4.4]non-1-en-4-one 2.1.1. 2-butyl-1,3-diazaspiro[4.4]non-1-en-4-one chlorhydride Title compound is prepared as described in step 1.2 from ethyl 1-amino-1-cyclopentylcarboxylate.

2.1.2. 2-butyl-3-[[2-[2-[1(or 2)-(triphenylmethyl)-1(or 2)H-tetrazol- 5-yl]phenyl]-6-quinolyl]methyl]-1,3-diazaspiro[4.4] non-1-en-4-one 1 g (7.24 mmol) of potassium carbonate and 1.25 g (1.64 mmol) of the 80% pure [sic] compound obtained in step 1.1 are added to 0.35 g (1.52 mmol) of compound obtained in step 2.1.2 dissolved in 6 ml of dimethylformamide. The reaction mixture is left stirring at room temperature overnight. It is taken up with water and extracted with toluene.

The organic phase is recovered, the solvent is evaporated off and the organic phase [sic] is dried over magnesium sulfate. The residue is purified by chromatography on a column of silica gel, eluting with a toluene/ethyl acetate (85:15) mixture.

0.8 g of the expected product is obtained.

2.2. 2-butyl-3-[[2-[2-(1H-tetrazol-5-yl)phenyl]-6-quinolyl] methyl]-1,3-diazaspiro[4.4]non-1-en-4-one 20 ml of a methanol/acetic acid (90:10) mixture containing 0.8 g of the compound obtained above in step 1.3 are heated to the refluxing temperature for 6 hours. The solvents are removed under reduced pressure and the residue is crystallized in ether.

0.3 g of product is obtained.

NMR d [sic] 0.8 (t, 3H), 1.17–1.37 (m, 2H), 1.38–1.62 (m, 2H), 1.62–2 (m, 8H), 2.4 (t, 2H), 4.95 (s, 2H), 7.55 (d, 2H), 7.6–8 (m, 6H) , 3.5 (d, 1H) , 16.2–16.6 (unresolved complex, 1H ).

EXAMPLE 3

2-butyl-3-[[2-[2-(1H-tetrazol-5-yl)phenyl]-6-quinolyl] methyl]-1,3-diazaspiro [4,5]dec-1-en-4-one 3.1. 2-butyl-3-[[2-[2-[1(ou 2)-(triphenylmethyl)-1(ou 2)H-tetrazol-5-yl)phenyl]-6-quinolyl]methyl]-1,3-diazaspiro[4,5] dec-1-en-4-one 3.1.1. 2-butyl-1,3-diazaspiro[4,5]dec-1-en-4-one A mixture of 11,3 g (8,8 mmol) of ethyl pentanimidate and of 11,56 g (6,7 mmol) of ethyl 1-amino-1-cyclopentylcarboxylate in 100 ml of xylen containing 0,6 ml of acetic acid is heated to refluxing temperature. Then reaction mixture is allowed to cool, residue is eliminated by filtration and solvent evaporated under reduced pressure. Title compound cristallized in ether.

Melting point=124°–125° C.

3.1.2. 2-butyl-3-[[2-[2-[1(or 2)-(triphenylmethyl)-1(or 2)H-tetrazol- 5-yl)phenyl]-6-quinolyl]methyl]-1,3-diazaspiro[4,5]dec-1-en-4-one 1,64 g (7,88 mmol) of compound obtained in step 3.1.1, 3 g (21,7 mol) of potassium carbonate and 5 g (7,47 mmol) of the 90% pure compound obtained in step 1.1 are added to 25 ml of dimethylformamide. The reaction mixture is left stirring at room temperature overnight and is poured into 100 ml of water. After filtration, the residue is purified by chromatography on a column of silica gel eluting with a toluen/ethyl acetate (80:20) mixture.

2,3 g of the expected product is obtained in the form of a gum.

3.2. 2-butyl-3-[[2-[2-(1H-tetrazol-5-yl)phenyl]-6-quinolyl] methyl]-1,3-diazaspiro[4,5]dec-1-en-4-one 20 ml of methanol/acetic acid (90:10) mixture containing 0,59 g (0,8 mmol) of the compound obtained above in step 3.1 are heating to the refluxing temperature for 5 hours. The solvents are removed under vacuum and the residue is cristalized in ether.

0,2 g of product are obtained.

Melting point=122°–123° C.

NMR: d 0,8(t,3H), 1,17–1,37(m,2H), 1,37–1,88 (unresolved complex, 12H) , 2,4(t,2H) , 4,9(s,2H), 7,5(d,2H), 7,6–8(m,6H), 8,35(d, 1H)

The table which follows illustrates the structures and physical properties of a few compounds according to the invention.

TABLE

| No | $R_1$ | $R_2$ | $R_3$ | Salt | MP (°C.) | NMR Data |
|----|-------|-------|-------|------|----------|----------|
| 1 | —$(CH_2)_3CH_3$ | —$CH_3$ | —$CH_3$ | — | | d 0,77(t, 3H), 1,15–1,42(m, 8H), 1,5(m, 2H), 2,38(m, 2H), 4,9(s, 2H), 7,6(d, 2H), 7,6–8(m, 6H), 8,37(d, 1H), 16,2–16,6(unresolved complex, 1H) |
| 2 | —$(CH_2)_3CH_3$ | —$CH_2CH_3$ | —$CH_2CH_3$ | — | | d 0,62(t, 6H), 0,85(t, 3H), 1,22–1,42(m, 2H), 1,45–1,6(m, 2H), 1,67(q, 4H), 2,48(t, 2H), 4,9(s, 2H), 7,5–8(m, 8H), 8,3(d, 1H) |
| 3 | —$(CH_2)_3CH_3$ | —$(CH_2)_2$— | | — | | d 0,77(t, 3H), 1,17–1,4(m, 2H), 1,42–1,75(m, 6H), 2,5(t, 2H), 4,98(s, 2H), 7,5–8(m, 8H), 8,3(d, 1H), 16,2–16,6(unresolved complex, 1H) |
| 4 | —$(CH_2)_3CH_3$ | —$(CH_2)_2$— | | 2 HCl | 128 (dec) | |
| 5 | —$(CH_2)_3CH_3$ | —$(CH_2)_4$— | | — | | d 0,8(t, 3H), 1,17–1,37(m, 2H), 1,38–1,62(m, 2H), 1,62–2(m, 8H), 2,4(t, 2H), 4,95(s, 2H), 7,55(d, 2H), 7,6–8(m, 6H), 3,5(d, 1H), 16,2–16,6(unresolved complex, 1H) |
| 6 | —$(CH_2)_3CH_3$ | —$(CH_2)_5$— | | — | 122–123 | d 0,8(t, 3H), 1,17–1,37(m, 2H), 1,37–1,88(unresolved complex, 12H), 2,4(t, 2H), 4,9(s, 2H), 7,5(d, 2H), 7,6–8(m, 6H), 8,35(d, 1H) |

Legend of the table
in column "Salt" 2 HCl represents dihydrochloride
in colum "MP (°C.)" "dec" signifies decomposition
$^1$H NMR measured at 200 MHz in dimethyl sulfoxide.

The compounds of the invention were subjected to pharmacological studies which demonstrated their angiotensin II-antagonist properties.

Test of binding of [³H]angiotensin II to rabbit adrenal cortex

Male Fauve de Bourgogne rabbits weighing 2 to 3 kg are used. After sacrifice by cervical dislocation, the adrenal glands are excised and the cortex is dissected on a culture dish cooled in ice. It is placed in 10 ml of an ice-cold 10 mM tris(hydroxymethyl)aminomethane buffer solution containing 0.33M sucrose and 1 mM ethylenediaminetetraacetic acid and whose pH has been adjusted to 7.4 with hydrochloric acid. The tissue is homogenized using an electrical Potter apparatus with 13 to-and-fro movements of the plunger at a speed of 1200 rpm. The volume of the preparation is adjusted to 25 ml with Tris-sucrose buffer before centrifuging for 15 min at 1075×g. The supernatant is retained. The pellet is homogenized again, after resuspension in 10 ml of Tris-sucrose buffer, by transfer to the electrical Potter, and then centrifuged under the conditions described above. The supernatant obtained is added to the first, and they are centrifuged for 30 min at 47,800×g. The pellets are finally taken up with 150 volumes (equivalent to 100 mg of tissue in 15 ml of buffer) of a 50 mM Tris-HCl buffer solution containing 150 mM NaCl, 5 mM ethylenediaminetetraacetic acid, 1.25 µg/ml of bacitracin, 100 µM phenylmethylsulfonyl fluoride and 0.2% of bovine serum albumin (pH=7.4 at 25° C.).

This suspension contains the microsomes of the adrenal cortex, and will be used as it is in the studies described below.

100 µl aliquot fractions of suspension are incubated in the presence of [³H]angiotensin II (New England Nuclear, specific activity 61 Ci/mmol) in a final volume of 1 ml of Tris-HCl buffer whose composition has been described above. After incubation for 30 minutes at 25° C., the microsomes are recovered by filtration on 0.45 µm Millipore HAWP™ cellulose nitrate filters conditioned beforehand by immersion in a 1% solution of bovine serum albumin. The filters are washed three times with 5 ml of ice-cold Tris-HCl buffer. The quantity of radioactivity bound to the tissues and retained on the filters is measured by scintillation spectrometry.

Non-specific binding of [³H]angiotensin II is measured by incubation in the presence of 1 µm non-radioactive angiotensin II. This non-specific binding represents 5 to 10% of the total quantity of radio-activity bound to the filter. The non-specific binding is the difference between the total radioactivity collected on the filter and the non-specific binding. The binding of [³H]angiotensin is measured in the presence of different concentrations of test compounds, and the $IC^{50}$, the concentration of the test compound which inhibits 50% of the specific binding of [³H]angiotensin II, is determined graphically.

The $IC_{50}$ concentrations of the compounds of the invention are less than 50 nM.

Inhibition of the response to angiotensin II on rat arterial blood pressure

Male rats (Sprague-Dawley, Charles River France) weighing 250 to 280 g are used, the rats being anesthetized with pentobarbital sodium (55 mg/kg i.p.) and maintained under artificial respiration (Harvard™ Respirator: respiration rate 70 ml per minute, air volume 12 ml per 100 g of body weight). The animals are "pithed" using a metal rod introduced via the orbit of the right eye and inserted over the length of the vertebral column. The left and right vagus nerves are sectioned (bilateral vagotomy); the right carotid artery is ligated, the left carotid artery being catheterized in order to measure the arterial blood pressure using a pressure cell (Statham™ type P23Db). A femoral vein is catheterized for the purpose of administration of various compounds.

The changes in mean arterial blood pressure induced by angiotensin administered intravenously at a dose of 0.5 µg/kg before the administration of the compounds of the invention, and those induced by angiotensin administered under the same conditions 5 minutes after the intravenous administration of the compounds of the invention or 30 minutes after the oral administration thereof, are measured. The compounds of the invention are administered at doses ranging from 0.01 to 100 mg/kg.

The percentage inhibition of the control response to angiotensin II is used in order to assess the angiotensin II-antagonist potential of the compounds of the invention.

The compounds of the invention or their suitable salts may be used for the treatment of various forms of hypertensive pathologies and of cardiac, renal or pulmonary insufficiencies, as well as for the treatment of glaucoma.

The compounds of the invention or their suitable salts may also be used in combination with other substances having cardiovascular activity, such as diuretics, α-blockers, β-blockers, calcium antagonists or angiotensin I-converting enzyme inhibitors.

The compounds of the invention or their suitable salts may be presented in all pharmaceutical forms suited to the treatment, for oral, parenteral, intramuscular or rectal administration: tablets, capsules including hard gelatin capsules, sterile solutions or suspensions, suppositories, and the like.

For the treatment of glaucoma, the compounds of the invention may be presented in the form of tablets, hard gelatin capsules, injections or topical ocular formulations.

The compounds of the invention may be administered to patients in a quantity which can range from 1 to 1000 mg per day per patient, in one or more doses.

We claim:

1. Derivatives of 3-(6-Quinolylmethyl)-4H-imidazol-4-one corresponding to the formula (I):

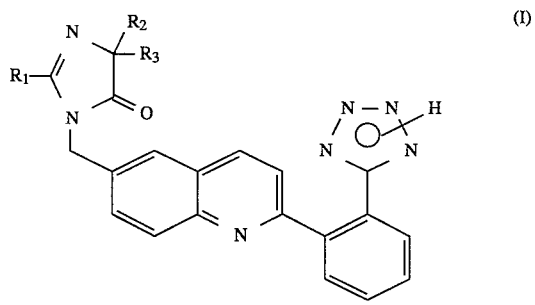

in which:
R₁ represents an unbranched or branched (C₂–C₅) alkyl group,
R₂ and R₃ represent, each independently of one another, either a hydrogen atom, or an unbranched or branched (C₁– C₅) alkyl group,
or R₂ and R₃ with the imidazole ring is a spirocyclo(C ₃–C₅)alkyl group,
and their addition salts with pharmaceutically acceptable acids and bases.

2. Derivatives according to claim 1, wherein
R₁ represents an unbranched or branched (C₂–C₅) alkyl group, $R_2$ and $R_3$ represent, each independently of one another, an unbranched or branched $(C_1-C_5)$alkyl group, or $R_2$ and $R_3$ with the imidazole ring is a spirocyclo$(C_3-C_8)$alkyl group.

3. Derivatives according to claim 2, wherein $R_1$ represents a butyl group, $R_2$ and $R_3$ represent, each independently of one another, an unbranched or branched $(C_1-C_5)$alkyl group, or $R_2$ and $R_3$ with the imidazole ring is a spirocyclo $(C_3-C_8)$alkyl group.

4. 5-butyl-6-[[2-[2-(1H-tetrazol-5-yl]phenyl)-6-quinolyl]methyl]-4,6-diazaspiro[2.4]hept-4-en-7-one.

5. 2-butyl-3-[[2-[2-(1H-tetrazol-5yl)phenyl]-6-quinolyl]methyl]-1,3-diazaspiro[4.4]non-1-en-4-one.

6. 2-butyl-3-[[2-[2-(1H-tetrazol-5-yl)phenyl]-6-quinolyl]methyl]-1,3-diazaspiro[4,5]dec-1-en-4-one.

7. Pharmaceutical composition, comprising a compound according to claim 1, in combination with a suitable excipient.

8. Derivatives corresponding to the formula (IX)

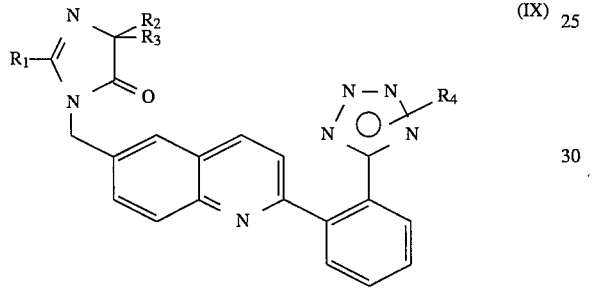

(IX)

in which:

$R_1$ represents an unbranched or branched $(C_2-C_5)$alkyl group, $R_2$ and $R_3$ represent, each independently of one another, either a hydrogen atom, or an unbranched or branched $(C_1-C_5)$alkyl group, or or $R_2$ and $R_3$ with the imidazole ring is a spirocyclo$(C_3-C_8)$alkyl group, and $R_4$ represents a group of formula $CR_5R_6R_7$ where $R_5$, $R_6$ and $R_7$ are, each independently of one another, a $(C_1-C_2)$alkyl group or a phenyl.

* * * * *